(12) United States Patent
Clifford et al.

(10) Patent No.: US 9,132,039 B2
(45) Date of Patent: Sep. 15, 2015

(54) DISPOSABLE ABSORBENT MOISTURE MANAGEMENT DRESSING

(71) Applicant: Principle Business Enterprises, Inc., Dunbridge, OH (US)

(72) Inventors: Alan A. Clifford, Marion, OH (US); Andrew J. Szypka, Curtice, OH (US); Erin L. Johnson, Perrysburg, OH (US); Judith L. Borcherdt, Sylvania, OH (US)

(73) Assignee: Principle Business Enterprises, Inc., Dunbridge, OH (US)

( * ) Notice: Subject to any disclaimer, the term of this patent is extended or adjusted under 35 U.S.C. 154(b) by 202 days.

(21) Appl. No.: 13/852,311

(22) Filed: Mar. 28, 2013

(65) Prior Publication Data

US 2013/0261587 A1 Oct. 3, 2013

Related U.S. Application Data

(60) Provisional application No. 61/617,087, filed on Mar. 29, 2012.

(51) Int. Cl.
| | |
|---|---|
| *A61M 27/00* | (2006.01) |
| *A61M 1/00* | (2006.01) |
| *A61F 13/15* | (2006.01) |
| *A61F 13/00* | (2006.01) |
| *A61F 13/53* | (2006.01) |
| *A61F 13/45* | (2006.01) |

(52) U.S. Cl.
CPC ..... *A61F 13/00021* (2013.01); *A61F 13/00063* (2013.01); *A61F 13/53* (2013.01); *A61F 2013/00097* (2013.01); *A61F 2013/00412* (2013.01); *A61F 2013/4587* (2013.01); *A61F 2013/530437* (2013.01)

(58) Field of Classification Search
CPC .......... A61F 2013/00097; A61F 2013/530437; A61F 2013/4587; A61F 13/53
USPC .......................... 604/319, 543, 378, 379, 380
See application file for complete search history.

(56) References Cited

U.S. PATENT DOCUMENTS

| | | | |
|---|---|---|---|
| 4,080,963 A | 3/1978 | Merry | |
| 4,871,812 A | 10/1989 | Lucast | |
| 4,917,112 A | 4/1990 | Kalt | |
| 4,960,594 A | 10/1990 | Honeycutt | |
| 5,000,741 A | 3/1991 | Kalt | |
| 5,056,510 A | 10/1991 | Gilman | |
| 5,072,687 A | 12/1991 | Mitchell | |
| 5,106,362 A | 4/1992 | Gilman | |
| 5,167,613 A | 12/1992 | Karami | |
| 5,180,375 A | 1/1993 | Feibus | |

(Continued)

*Primary Examiner* — Jacqueline Stephens
(74) *Attorney, Agent, or Firm* — Emch, Schaffer, Schaub & Porcello, Co., L.P.A.

(57) ABSTRACT

A disposable, absorbent "moisture management" drain pad for use on IV sites, tracheotomy tube sites, chest tube sites, catheter sites, g-tube sites, and drain sites. The pads will protect drain sites/skin area around drain sites from exudates/drainage by absorbing large amounts of fluid and locking it into a super absorbent core that remains dry on the outer surface next to the skin/drain site. The drain pad will contain an ultra-thin core containing super absorbent polymer and two layers of tissue substrates, a water impervious hydrophobic non-woven back sheet and a water pervious (hydrophilic) non-woven top sheet. Various materials can be substituted for these listed as long as they perform the required criteria need for the material.

16 Claims, 4 Drawing Sheets

(56) References Cited

U.S. PATENT DOCUMENTS

| | | |
|---|---|---|
| 5,244,457 A | 9/1993 | Karami |
| 5,308,313 A | 5/1994 | Karami |
| 5,358,492 A | 10/1994 | Feibus |
| 5,549,584 A | 8/1996 | Gross |
| 5,836,970 A | 11/1998 | Pandit |
| 6,004,253 A | 12/1999 | Riedel |
| 6,290,685 B1 | 9/2001 | Insley |
| 6,420,622 B1 | 7/2002 | Johnston |
| 6,548,727 B1 | 4/2003 | Swenson |
| 6,765,122 B1 | 7/2004 | Stout |
| 6,867,342 B2 | 3/2005 | Johnston |
| 6,881,875 B2 | 4/2005 | Swenson |
| 6,910,581 B2 | 6/2005 | McMichael |
| 6,977,323 B1 | 12/2005 | Swenson |
| 7,093,598 B1 | 8/2006 | Hanneman |
| 7,285,576 B2 | 10/2007 | Hyde |
| 7,410,477 B2 | 8/2008 | Gomez |
| 7,563,734 B2 | 7/2009 | Gleason |
| 7,777,090 B2 | 8/2010 | Park |
| 7,777,091 B2 | 8/2010 | Park |
| 7,781,639 B2 | 8/2010 | Johnston |
| 7,858,838 B2 | 12/2010 | Holm |
| 7,910,790 B2 | 3/2011 | Johnston |
| 7,955,636 B2 | 6/2011 | Terry |
| 7,988,673 B2 * | 8/2011 | Wright et al. ................. 604/174 |
| 8,057,446 B2 | 11/2011 | Kane |
| 8,100,872 B2 | 1/2012 | Patel |
| 2004/0082925 A1 | 4/2004 | Patel |
| 2007/0082036 A1 | 4/2007 | Dixon |
| 2010/0154822 A1 | 6/2010 | Reed, Jr. |
| 2010/0318052 A1 | 12/2010 | Ha |
| 2011/0112457 A1 | 5/2011 | Holm |
| 2011/0112458 A1 | 5/2011 | Holm |

* cited by examiner

DISPOSABLE ABSORBENT MOISTURE MANAGEMENT DRESSING

CROSS REFERENCE TO RELATED APPLICATIONS

This application claims the benefit of provisional patent application No. 61/617,087 filed on Mar. 29, 2013.

BACKGROUND OF THE INVENTION

The present invention relates to a disposable absorbent moisture management pad of the kind which is intended for daily use and comprises of a non-woven top sheet, an absorbent core containing Gelok super absorbent laminate, a fluid impervious back sheet non-woven that covers at a minimum the absorbent core, and an insertion slit and fixation/positioning hole for tubes. The design of the pad is such that the pads can be treated with an antimicrobial and be sterile if needed.

Currently, there are many absorbent gauze/sponges being produced and used for absorbent dressings around g-tubes, tracheotomy tubes, IV sites etc. These products all lack the ability to absorb fluid and to lock the fluid into the core so that the skin remains dry, clean, and free of contaminations. The pad of the present invention will absorb wound leakage while maintaining a dry surface on the skin. The skin will remain healthy and the wearer will see a decrease in unhealthy skin issues relating to moisture accumulation.

SUMMARY OF THE INVENTION

A disposable, absorbent "moisture management" drain pad is disclosed for use on IV sites, tracheotomy tube sites, chest tube sites, catheter sites, g-tube sites, and drain sites. The pads will protect drain sites/skin area around drain sites from exudates/drainage by absorbing large amounts of fluid and locking it into a super absorbent core that remains dry on the outer surface next to the skin/drain site. The super absorbent laminate of the core is very effective at controlling or reducing odor. The high percentage of super absorbent polymer in the core functions to contain odors in the core area of the dressing. The drain pad will contain an ultra-thin core containing super absorbent polymer and two layers of tissue substrates, a water impervious hydrophobic non-woven back sheet and a water pervious (hydrophilic) non-woven top sheet. Various materials can be substituted for the materials listed as long as they perform the required criteria need for the material.

Other objects and advantages of the present invention will become apparent to those skilled in the art upon a review of the following detailed description of the preferred embodiments and the accompanying drawings.

BRIEF DESCRIPTION OF THE DRAWINGS

FIG. 5 is a cross sectional view taken along line 5-5 in FIG. 1.

DETAILED DESCRIPTION OF THE PREFERRED EMBODIMENT

The invention is directed to a dressing that can be used on a patient. More particularly the dressing is designed to be used with a gastric tube or other tube that is inserted into a patient. The dressing is designed to collect fluids from the patient at the site where the tube is positioned in the patient. The dressing utilizes a supper absorbent polymer to retain the fluids from the patient and to produce a dressing that is very thin in size but capable of retaining a large quantity of fluid. The features of the invention will be more readily understood by referring to the attached drawings in connection with the following description.

Figure 1:
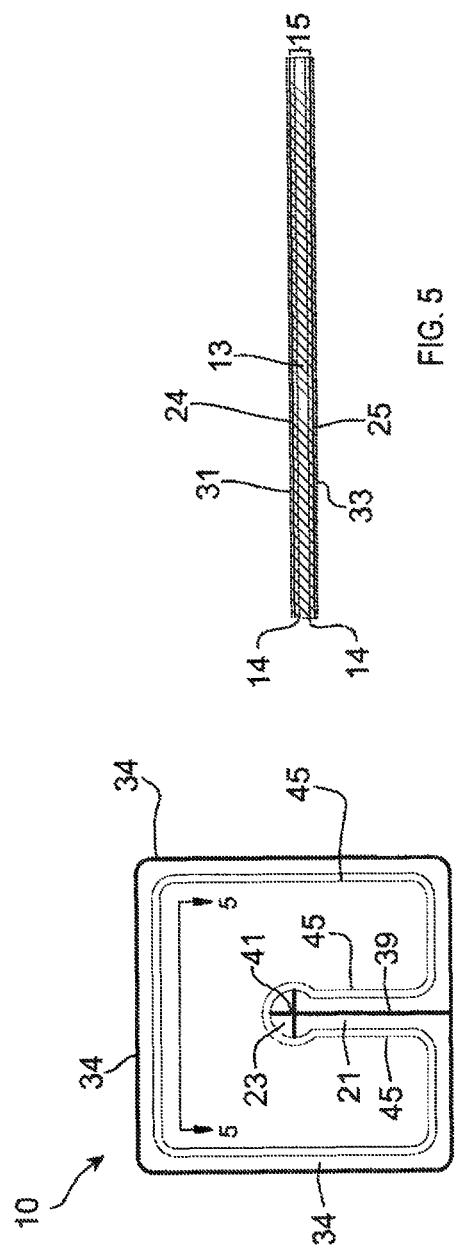
FIG. 1 is a top view of the dressing of the present invention.
Figure 2:
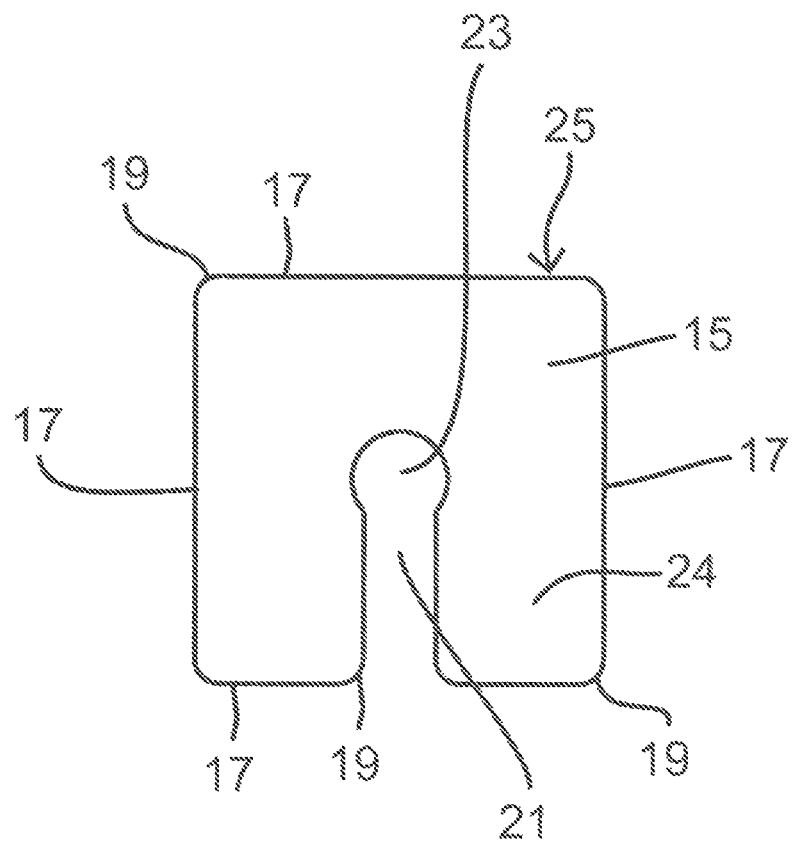
FIG. 2 is a top view of the super absorbent core of the dressing.

The features of the dressing 10 are shown in FIGS. 1-7. The dressing has a core 15 that is a laminate of a super absorbent polymer and tissue. The Gelok laminate material is an example of a laminate that works particularly well for the core. The core has a super absorbent polymer powder 13 that is positioned between two layers of cellulosic tissue 14. This paper like super absorbent core 15 has high fluid absorbency, but remains dry to the touch. The super absorbent laminate of the core is very effective at controlling or reducing odor. The high percentage of super absorbent polymer in the core functions to contain odors in the core area of the dressing. The super absorbent material encapsulates or encloses the fluids from the patient, including the odor producing components of the fluid. Thus, the odors from the fluids are primarily retained in the super absorbent laminate and less odor producing components escape to the air adjacent the patient. The core 15 has a thickness from about 20 mils to about 36 mils. The core 15 has an outer perimeter 17 that generally defines the outer limits of the core 15. The core 15 as shown in FIG. 2 is depicted as being substantiality square in shape with rounded corners 19. It should be appreciated, however, that other shapes such as circles, rectangles and other configurations can be used for the core 15. An opening 23 is positioned substantially in the center of the core 15. The opening 23 is designed to fit in close proximity around a tube 27 that is positioned in an opening in a patient. An example of a tube that can be used in connection with the dressing 10 is a gastric tube that is used to provide nourishment to a patient. The core 15 has a channel 21 that extends form the opening 23 to the outer perimeter 17 on one side of the core 15. The channel 21 is designed to have a width that is slightly smaller then the diameter of the opening 23 in the core 15. It should be appreciated that the opening 23 and channel 21 can be sized to be used with particular sizes of tubes that are inserted into the patient. The opening just needs to be wide enough to allow the tube used with the patient to pass through the opening and part of the core material can be displaced as the tube passes through the opening. It is important that the opening 23 it relatively snuggly around the tube and that the channel 21 can be used as a passageway for positioning the tube in the opening. The material of the opening can be displaced to snugly fit around various sizes of tubes that are used with a patient. The core has a first side 24 and a second side 25 wherein the first side 24 or the second side 25 can be positioned adjacent the body of the patient in the area of the tube 27.

Figure 4:
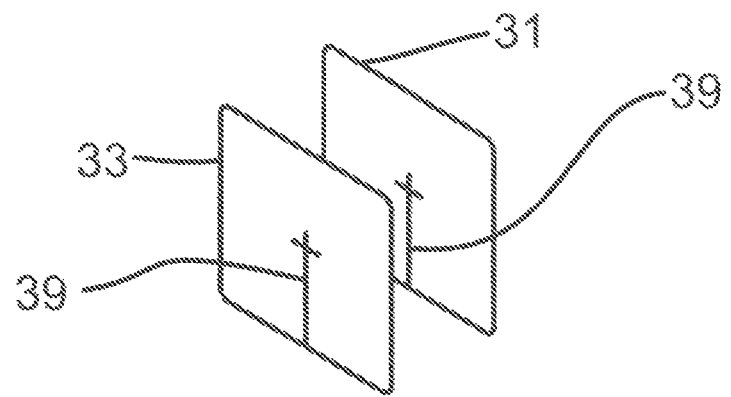
FIG. 4 is a perspective view of the non-woven layers.
Figure 3:
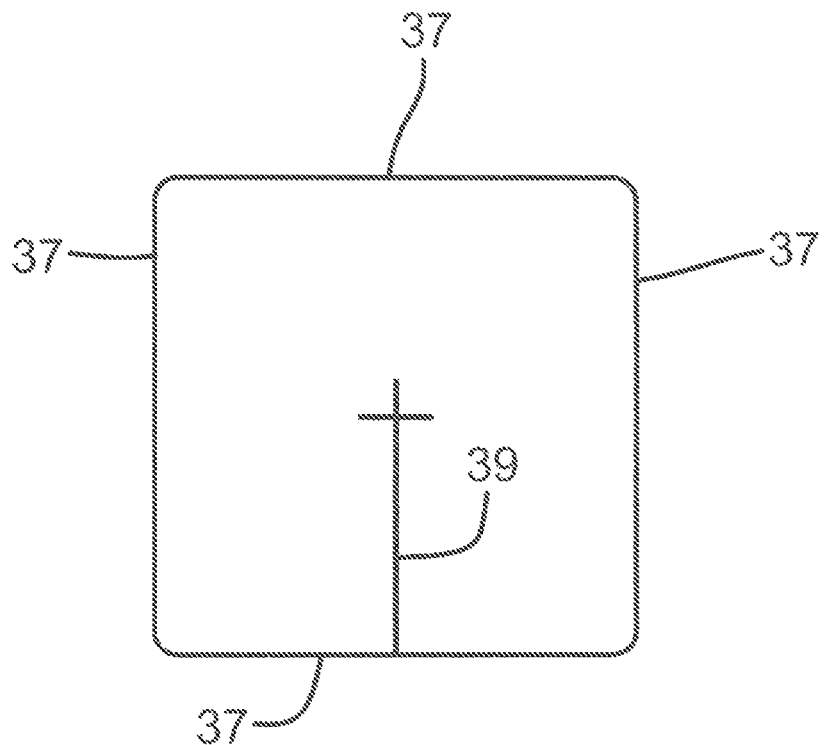
FIG. 3 is a top view of the outer non-woven layer of the dressing.
Figure 6:
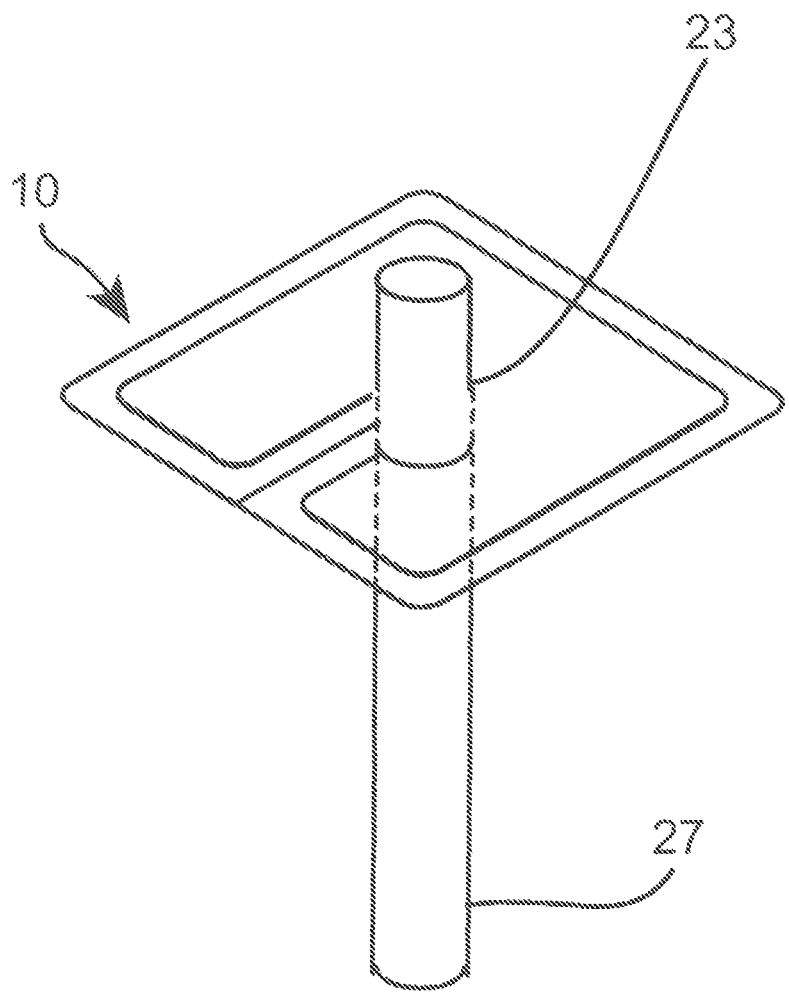
FIG. 6 is a perspective view of the dressing being positioned on a table.

As shown in FIGS. 3 and 4 there is a first layer 31 of non-woven material is positioned on the first side 24 of the core 15. A second layer 33 of non-woven material is positioned adjacent the second side 25 of the core 15. The first and second layer are preferably a spun bond-melt blown-spun bond polypropylene (SMS) non-woven material having a thickness from about 2 mils to about 10 mils and a basis weight from about 5 gsm to about 15 gsm. Other materials such as a film can be used for the second layer. The second layer 33 can also have a surface that faces away from the core that is printable. The first and second layers of non-woven material have an outer peripheral boundary 37 and the outer peripheral boundary of the first and second levers extends beyond the outer peripheral edge of the core 15. The first and second layers of non woven material define a slot 39 that is in alignment with the channel 21 and the opening in the core 15. The slot 39 on the first layer 31 and the slot 39 on the second layer 33 are substantial alignment with each other. A slit 41 is positioned on the slot 39 on the first and second layers of non-woven material. The slit 41 is positioned substantially perpendicular to the slot 39 and the slit is in alignment with the opening 23 in the core 15. The material of the first and second layers adjacent the slot and the slit can be displaced by the tube 27.

A seal 45 is formed between the first and second layers of non-woven material. The seal can be made by heat sealing, ultrasonic bonding or by an adhesive. The seal must be sufficiently strong to retain its integrity as the super absorbent core expands when it absorbs fluids. The seal 45 is positioned adjacent the outer boundary of the first and second layers 31, 33 of non-woven material. The seal 45 also extends along the portion of the first and second layers that is adjacent the channel 21 and the opening 23. The seal 45 is formed so that the entire core 15 is positioned inside the confines of the seal 45. An edge margin 34 of non-woven material of the first and second layers extends beyond the seal 45 in a direction away from the core 15.

The first layer 31 of non-woven material is designed to wick fluid from the patient, in the area adjacent to the tube 27, to the super absorbent laminate material in the core 15. The first and second layers are usually a hydrophilic non-woven material as this works very well as a wicking layer. The second layer 33 of non-woven material can also be designed to function to wick material away from the patient to the super absorbent material in the core 15. It is also possible that the second layer 33 of non-woven material can be fluid impervious material that is designed to act as a fluid barrier and to retain fluids from the patient in the core 15. The material of the second layer 33 can be a hydrophobic material that resists fluids and is generally impervious to the flow of fluids. It is preferable that the impervious second layer 33 be breathable to provide as comfortable as an environment for the patient.

The seal 45 is designed to retain fluids from the patient in the core 15. The super absorbent polymer contained in the core is designed to absorb and retain large quantities of fluids. Accordingly, the dressing 10 will be capable of wicking fluids away from the site of the tube 27 into the core 15 of the dressing 10 where the fluids will be retained in the super absorbent polymer. The super absorbent laminate of the core is very effective at controlling or reducing odor. The high percentage of super absorbent polymer in the core functions to contain odors in the core area of the dressing. It is also possible that an odor control substance can be incorporated into the material of the core to control odors from the fluids from the patient. Odor control agents such as baking soda, activated carbon and other known agents can be dispersed in the super absorbent polymer of the core. The absorption qualities of the super absorbent polymer contained in the core 15 allow the dressing 10 to be relatively thin, but at the same time manage a significantly large quantity of fluids that seep from the opening where the tube 27 is positioned. The core 15 manages the fluids from the patient by absorbing and retaining the fluids. This feature of the core reduces breakdown of the skin adjacent the tube, reduces odor issues and reduces the frequency that pads need to be changed. The thinness of the dressing 10 provides a more comfortable and anesthetically pleasing dressing in the area of the tube 27. In practice it has been found that the thickness of the dressing can be less then 30 mils and still function to manage fluids that leak from an opening in the patient where the tube 27 is positioned. The dressing pad is usually from about 20 mils to about 50 mils in thickness.

The typical overall dimensions of the pad will be 5.0 inches×5.0 inches. This provides a pad that will provide coverage for most drain applications. The absorbent core dimensions would be 4.25 inches×4.25 inches. Pad dimensions can be varied to accommodate larger or smaller drain areas. The drain pad also incorporates a unique "tube insertion slit/positioning-fixation hole" design that allow various sized tubes, the diameter of the tubes, to be used with the pad. The tube positioning hole defined by the slot 39 and the slit 41 will gently fit around the tube and hold it in position even when the pad is saturated with fluid.

The other key feature of this unique design is the pads ultra-thin core that is made with super absorbent powder and cellulosic tissues. This material is a super absorbent laminate made by Gelok International. This paper like, super absorbent core allows for high fluid absorbency with an ultra-dry sensation on the exterior of the core. Accordingly, the pad feels much drier when contacted by a patient or a care giver for the patient. The pad does not rewet as much as the prior art pads when handled. The pads of this invention have at least 50 times less rewetting then the prior gauge/foam pads. The dressing can also be sterilized if desired.

In operation a tube 27 is positioned in an opening in a patient to provide nourishment, to provide medication, to remove substances from the patient and for other well known medical uses. In almost all applications the opening in the patient where the tube is positioned will leak or secrete fluids. It is very important that the fluids that leak or secreted from the opening are managed to maintain the opening in as healthy a condition as possible. The dressing 10 of the present invention can be positioned around the tube 27 by passing the tube through the channel 21 the slot 39 and the slit 41 to position the tube in the opening 23. The channel 21 is usually positioned so that it is directed upwardly on the patient. The edge margin 34 of non-woven material can be gripped and used to position the dressing 10 around the tube 27. The pad of this invention has a stiffness from the component layers that assist in positioning the pad on the patient. The stiffness of the pad helps the pad retain its shape when the pad is removed which makes it easier to remove the pad. The stiffness of the pad also allows the pad to retain its shape and position on the patient as the pad absorbs fluids from the patient. The pad has a bending length stiffness from about 50 to about 60. This is about 30 times stiffer than the gauge/foam pads presently being used. As an example, the pad of the current invention will extend from a horizontal surface approximately 4.5 inches to reach a 45° angle of deflection. The prior art gauze pad will extend approximately 2.5 inches when it is at a 45° angle of deflection. Accordingly, the current invention is much stiffer than the prior art gauze pad. The edge margin 34 is outside of the seal 45 and is not exposed to the fluids that are absorbed and retained in the core 15. By using the edge margin to handle the pad, there is less possibility of contamination from the fluids that are absorbed and retained in the core 15. The first layer 31 of non-woven material will come into contact with any fluids that are produced by the opening and wick the fluids to the super absorbent polymer in the core 15. The super absorbent polymer will absorb and retain the fluids within the core 15. The super absorbent laminate of the core is very effective at controlling or reducing odor. The high percentage of super absorbent polymer in the core functions to contain odors in the core area of the dressing. The core 15 can absorb and retain, in the super absorbent polymer, as much as 3 times the fluids that can be just absorbed by the currently used gauze/sponge type of products. The dressing 10 can also be worn or used for 6-10 hours due to the high absorptive properties of the super absorbent polymer material and this is considerably longer, 2-4 times, than the pads currently used. As the fluids are moved away from the area of the patient adjacent the opening, the opening will be kept dry and as healthy as possible. The collection of the fluids from the opening in the body will help to reduce infections and other wound healing issues that are frequently associated with a tube that is positioned in a patient. The second layer 33 of non-woven material can also be used to wick fluids or moisture into the super absorbent polymer in the core 15. The second layer 33 of non-woven material, can also be a fluid impervious material that will function to prevent any fluid in the core 15 from leaving the dressing 10 through the second layer 33. It is important, however, that the first and second layers of non-woven material be breathable to provide good air flow around the site where the tube is positioned in the body of the patient. The breathable good air flow characteristics of the first and second layer further provide a healthy environment in the area adjacent to the opening in the patient where the tube is positioned. An antimicrobial or antifungal agent can be incorporated into the first layer 31 of non-woven material to provide additional protection for the site of the opening in the patient where the tube is positioned. An antimicrobial and antifungal compound sold under the name AEG15 has been found to be very effective for this component of the pad, lithe dressing 10 is designed so that either the first or second layer of non-woven material can be positioned adjacent the patient, the second layer 33 of non-woven material can also contain an antimicrobial or antifungal agent.

Although it is anticipated that the dressing 10 will be designed so that there is one side, the first layer 31 of non-woven material, that is positioned against the patient, it is possible that the second layer 33 of non-woven material can also be designed to be positioned against the body of the patient. In this configuration the dressing can be applied without reference to the particular side of the dressing that is designed to be positioned adjacent to the patient.

Once the dressing has been in use for a sufficient period of time it can be easily changed by sliding to dressing from position around the tube 27 by having the tube move through the channel 21 and the slot 39. A new dressing can then be positioned around the tube 27 in the manner previously described. The edge margin 34 of material provides a preferred area to grasp the dressing for removal. The edge margin is outside of the area where the fluids are absorbed and provides a less contaminated area to grip the dressing during changing procedures. The fluids from the area around the opening in the body were the tube 27 is positioned are retained in the core 15 and the used dressing can be easily disposed of by the care provider. As the fluids are moved away from contact with the patient's body the area around the opening where the tube is positioned are kept in a healthy environment.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A dressing for use on a patient comprising:
   a core of super absorbent polymer, the super absorbent polymer being suspended in a tissue layer, the core having a first side and a second side;
   an opening defined in the core, the opening extending from the first side to the second side of the core, a channel extends from the opening to an outer peripheral edge of the core;
   a first layer of non-woven material positioned on the first side of the core;
   a second layer of non-woven material positioned on the second side of the core, the first and second layers having an outer peripheral boundary, the outer peripheral boundary extending beyond the outer peripheral edge of the core;
   a slot positioned in the first and second layers of non-woven material in alignment with the channel and the opening;
   a seal formed between the first and second layers of non-woven material adjacent the outer boundary of the first and second layers and along the portion of the first and second layers adjacent the channel and opening, the seal containing the entire core between the first and second layers of non-woven material.

2. The dressing of claim 1 wherein a slit is positioned on the portion of the slot that is in alignment with the opening, the slit being disposed substantially perpendicular to the slot.

3. The dressing of claim 2 wherein a gastric or other tube can be placed in the opening of the core.

4. The dressing claim 3 wherein the material of the slot and slit being designed to fit snuggly around the tube.

5. The dressing of claim 4 wherein the slot and slit in the first and second layers are disposed to allow the opening to be moved into alignment with the gastric tube.

6. The dressing of claim 1 wherein the first layer of non-woven material is designed to wick fluids from the patient to the super absorbent material.

7. The dressing of claim 6 wherein the second layer of non-woven material is designed to wick fluids from the patient to the core.

8. The dressing of claim 6 wherein the second layer of non-woven material is a fluid impervious material that is designed to retain fluids from the patient in the core.

9. The dressing of claim 1 wherein the seal is designed to retain fluids from the patient in the core.

10. The dressing claim 8 wherein the second layer is hydrophobic and breathable.

11. The dressing of claim 1 wherein the dressing has a thickness of less than 30 mils.

12. The dressing of claim 1 wherein an odor controls substance is dispersed in the core to control odor from fluids from the patient.

13. The dressing claim 1 wherein the first and second layers form an edge margin on the side of the seal that is spaced apart from the core.

14. The dressing of claim 1 wherein an antimicrobial and antifungal substance is dispersed in the first and second layers of non-woven material.

15. The dressing of claim 1 wherein the dressing has a bending length stiffness from about 50 mm to about 60 mm.

16. The dressing of claim 1 wherein the dressing has a thickness from about 20 mils to about 50 mils.

* * * * *